(12) United States Patent
Vanderheijden et al.

(10) Patent No.: US 6,322,793 B1
(45) Date of Patent: Nov. 27, 2001

(54) CHANNEL CATFISH VIRUS VACCINE

(75) Inventors: Nathalie Vanderheijden, Brussels; Joseph A. Martial, Esneux, both of (BE); Larry A. Hanson, Mississippi State, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 09/334,181

(22) Filed: Jun. 16, 1999

(Under 37 CFR 1.47)

Related U.S. Application Data

(60) Provisional application No. 60/089,608, filed on Jun. 17, 1998.

(51) Int. Cl.[7] .......................... A61K 39/245; C12N 7/01; C12N 7/04; C12N 15/869
(52) U.S. Cl. .................... 424/199.1; 424/205.1; 424/229.1; 424/817; 435/235.1; 435/236; 435/320.1
(58) Field of Search ................... 435/235.1, 236, 435/320.1; 424/199.1, 229.1, 205.1, 817; 800/8, 20

(56) References Cited

U.S. PATENT DOCUMENTS 4,219,543 * 8/1980 Hartmann et al. ................. 435/235.1
5,223,424 * 6/1993 Cochran et al. ..................... 435/236

OTHER PUBLICATIONS

Vanderheijden et al. Virology 218: 422–426, Apr. 1996.*
Zhang et al. Journal of Fish Diseases 19:121–128, 1996.*
Kancharla et al. Diseases of Aquatic Organisms 37:25–34, 1996.*
Zhang et al. Virology 209:658–663, 1995.*
The Audobon Society Nature Guides: Wetlands. 1985. W.A. Niering et al. Alfred A. Knopf, Inc., New York. p. 376.*

* cited by examiner

*Primary Examiner*—Mary E. Mosher
(74) *Attorney, Agent, or Firm*—Piper Marbury Rudnick & Wolfe, LLP; Steven B. Kelber

(57) ABSTRACT

An attenuated, avirulent recombinant vaccine providing challenged protection against channel catfish virus comprises deletion of gene 50. Gene 50 encodes a secreted glycoprotein. Removal of gene 50, or replacement of gene 50 with foreign genetic material, provides a vaccine with which induces virus specific immunity against CCV disease.

8 Claims, 3 Drawing Sheets

CHANNEL CATFISH VIRUS VACCINE

This application is a regular National application claiming priority from Provisional Application, U.S. Application Ser. No. 60/089,608 filed Jun. 17, 1998. The entirety of that provisional application is incorporated herein by reference.

BACKGROUND OF THE INVENTION

1. Field of the Invention

The invention of this application pertains to a vaccine for channel catfish virus, and in particular, a recombinant vaccine with gene 50 of the wild type or V60 channel catfish virus deleted or substantially deleted from the channel catfish virus. This invention also pertains to methods of vaccinating channel catfish against channel catfish virus, using the gene 50-deleted recombinant virus.

2. Background of the Prior Art

Channel catfish virus (CCV) (Ictalurid herpesvirus-1) is a cytopathic herpesvirus that can cause an acute, hemorrhagic, and lethal disease in the channel catfish Ictalurus punctatus (Fijan, 1968). Acute CCV epizootics in populations of fry and fingerling channel catfish can result in mortalities as high as 95% within one week (Plumb, 1978).

To date, three kinds of vaccines against CCV have been described in the literature. The first used a classically attenuated strain of the CCV Auburn strain (strain V60, Hartmann and Noga, 1980; Noga and Hartmann, 1981); the second was a subunit vaccine based on a preparation of viral envelope proteins (Awad et al. 1987); the third uses a live, thymidine-kinase-negative recombinant (Zhang and Hanson, 1995).

Considering the increasing importance of the channel catfish as a food source, the desirability of obtaining a vaccine for CCV to prevent the economic loss in hatcheries is evident. We studied the attenuated V60 strain, produced by multiple passages in cultured alternate host cells. The strain provides a protective vaccine strain against wild-type virus. When administered parenterally or as a water-borne vaccine, the strain was found to protect catfish fingerlings against a viral challenge, promoting a survival rate of over 90% (Walczak et al., 1981). A major deletion was found in gene 50 of the V60 strain (Vanderhejiden et al, 1996). Gene 50 encodes a secreted glycoprotein, highly glycosylated like the mucin-type glycoproteins, designated gp 250 (Vanderheijden, et al., 1999). Few viral glycoproteins are secreted upon herpesvirus infection (Randall et al 1980) and their function in the viral cycle by is still unclear. Since the attenuated V60 strain possesses a large deletion in its gene 50, the possibility exists that this gene could be responsible, at least in part, for the virulence of the wild-type strain. This possibility, therefore, offers a potential vaccine development route.

SUMMARY OF THE INVENTION

This invention includes, in its broadest embodiment, a recombinant channel catfish virus, with all or substantially all of gene 50 deleted. By substantially all is intended to include sufficient deletions so as to prevent, partially or totally the expression of the native secreted glycoprotein encoded by gene 50 of CCV. Within the invention, portions of either or both the 5' or 3' terminus of gene 50 may be retained, while retaining the attenuated characteristic of the inventive recombinant vaccine. Provided sufficient deletion has occurred to prevent expression of the glycoprotein, virulence of infection with the attenuated vaccine will be avoided, and the goal of the invention achieved.

In its broadest embodiment, the ORF for gene 50 is simply not present. It may be deleted entirely, or replaced with an avirulent sequence. In the invention described herein below, gene 50 was replaced with a detectable reporter gene, lacZ. Other reporter genes may be inserted in place of gene 50, or nuclear material encoding an innocuous protein may be included, provided it does not interfere with expression of the recombinant virus such that challenge protection is achieved by sufficiently high circulating antibody titer. Selection of appropriate inserts, or simple deletion of the gene 50 without replacement with other nuclear material, is within the scope of those of skill in the art given the disclosure herein below, and remains part of the invention.

DETAILED DESCRIPTION OF THE INVENTION

This invention resides in the discovery that deletion or replacement of gene 50 in CCV gives rise to an attenuated recombinant virus, such that infection of catfish, immature or otherwise, generates antibodies sufficient to give protection against challenge without significant mortality. Accordingly, the invention lies in the recombinant virus, vaccine comprising the same, and vaccinated catfish reflecting circulating CCV antibody titers sufficient to provide protection upon challenge with wt CCV. In the field, vaccination is most effectively achieved through water distribution, as in a water-borne vaccine, although parenteral administration may also be used, where practical. Administration is effectively achieved through methods employed in conventional vaccines, including the three CCV vaccines described above. The disclosures of Hartmann and Noga, 1980; Noga and Hartmann, 1981, Awad et al., 1989 and Zhang and Hanson, 1995 are incorporated herein by reference for this and all purposes.

While this invention is explained in more detail by the examples set forth below, it will be immediately apparent to those of ordinary skill in the art that the reporter gene used to replace the gene 50 sequence in the examples is a tool of convenience, to confirm effective ligation and transfection. Other reporter genes, genes that do not encode reporter or label molecules, and other substantive expression genes may by substituted for the reporter gene used in the examples set forth below, and remain within the scope of the invention. Similarly, simple deletion of gene 50, or substantial portion thereof, is within the practice of the invention and provides an effective, attenuated viral vaccination agent to provide protection against CCV challenge. It should be further noted that this vaccine is effective for use, and contemplated for use, in protection for both free-swimming and "ranch" or "farm" catfish.

EXAMPLES

Construction of the Recombinant CCVd150

To assess the role of gene 50 in the virulence of CCV, we constructed a recombinant virus in which gene 50 was completely deleted and replaced by a reporter gene. The recombinant CCV was constructed in two major steps as described below.

Step 1. Construction of the pUT50 Transfer Plasmid

Figure 1:
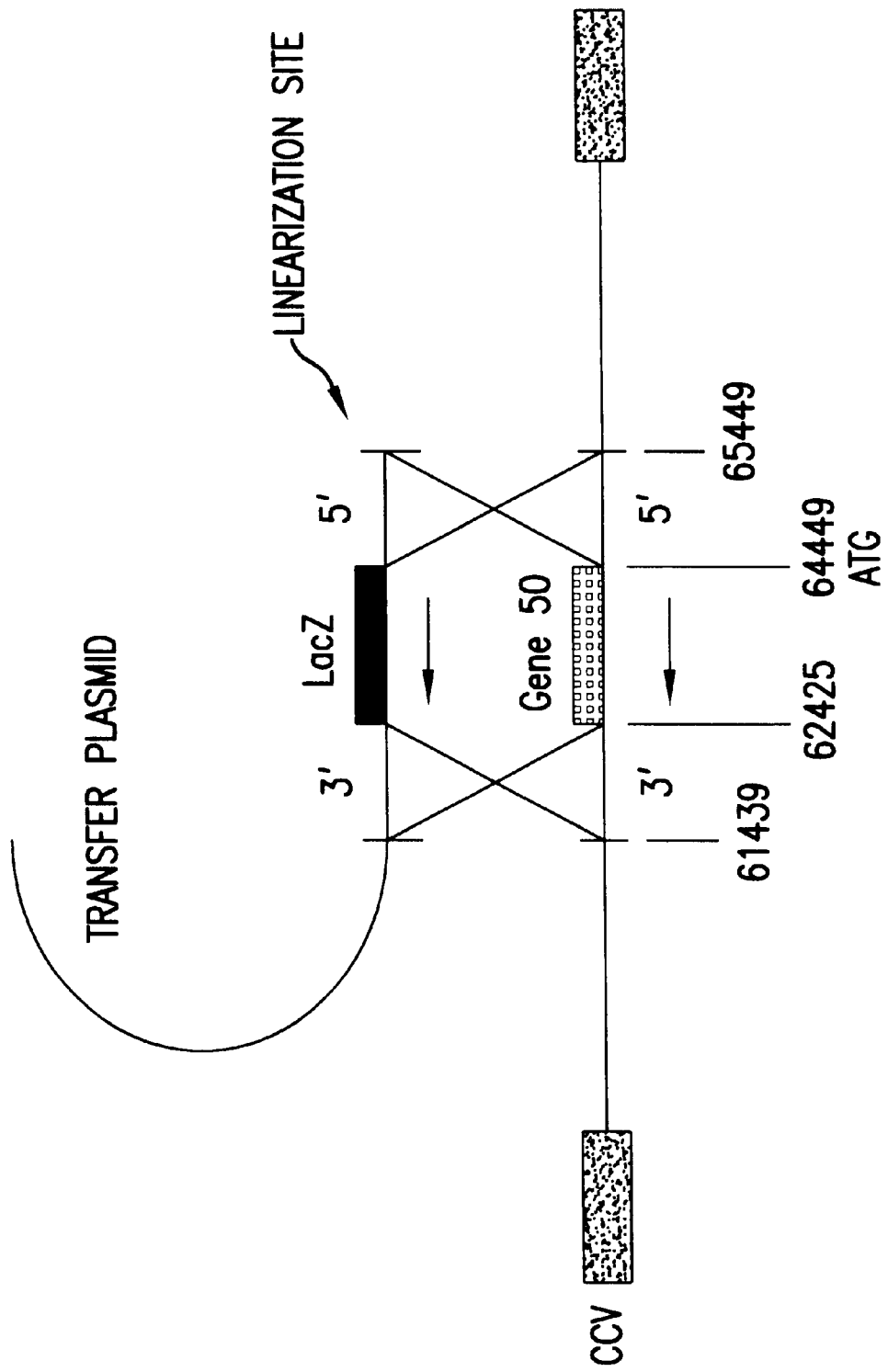
FIG. 1 is a schematic drawing of the construction of a gene 50 deleted recombinant channel catfish virus of the claimed invention.

The first step consisted in the construction of a transfer plasmid allowing the replacement of the viral gene 50 by the reporter lacZ gene of *E. coli* after homologous recombination between the plasmid and the viral DNA. To achieve this goal, we cloned the viral sequences flanking the coding sequence of gene 50 into a plasmid, such that the virus sequence upstream of gene 50 was in front of the lacZ gene of *E. coli* and the virus sequence downstream of gene 50 was behind (FIG. 1). This transfer plasmid allowed the complete removal of the coding sequence of gene 50 after homologous recombination with the viral DNA.

We amplified by the Polymerase Chain Reaction (PCR) 1 kilobasepair (kbp) of both flanking sequences of gene 50, spanning nucleotide (nt) 65449 to nt 64449 before the translational start codon (64448) and spanning nt 62425 to nt 61439 after the translational stop codon (62436). Two pairs of primers [SEQ ID NOS.:1–4](primer 5'-#1: 5'AATCTAGACCATGGATTATCAACACATGAACGTC3' and primer 5'-#2: 5'TTACTAGTTCGAGGTCAAGC-TACGGA3'; primer 3'-#1: 5'ATTAAGGGCCCTTGGCCG-GTGCGGCGAAG3' and primer 3'-#2: 5'ATTAAAGATCTAACCGCCCCCGCCGGAGA3') were chosen from the viral DNA sequence (Davison, 1992) (GenBank Accession No. M75136) to amplify respectively the 5' and 3' flanlkng regions of gene 50. Restriction sites were included in the primers to allow cloning procedure. The target viral DNA used for amplification was prepared as follows: BB cells (ATCC CCL59), a cell line derived from caudal trunk tissues of the Brown Bullhead (Ameiurus nebulosus) were grown at 28° C. in Glasgow minimum essential medium (MEM, Gibco BRL, U.S.A.) buffered with 23 mM Tris-HCl (pH 7.4) and supplemented with 4 mM sodium bicarbonate, 10% fetal bovine serum, 10% tryptose phosphate broth, 100 U/ml penicillin and 100 $\mu$g/ml streptomycin. The wild-type strain of CCV (Auburn 1 clone A) was obtained from the ATCC (VR-665). A viral stock at the second passage was produced by infecting a confluent monolayer of BB cells at a multiplicity of infection (MOI) of 0.01 in culture medium without fetal bovine serum. Infected cells were collected with the medium at 72 hours post-infection and pelleted by a 10 min. centrifugation at 600 g. Supernatant was divided into 1 ml aliquots and frozen at −70° C. Virus titer was determined by end-point dilution (Reed and Muench, 1938) and corresponded to $6.10^6$ TCID$_{50}$/ml. For PCR, one viral aliquot was incubated for 2 hours at 37° C. with 50 $\mu$g/ml proteinase K which was subsequently inactivated by heating the sample 10 min. at 100° C. PCR was performed using 10 $\mu$l of viral sample, 100 pmol of each primer (Eurogentec, Belgium), 1×buffer (75 mM Tris-HCl, pH 9.0, 20 mM $(NH_4)_2S_4$, 0.1% Tween20), 200 $\mu$M dNTPs, 2 units of Taq DNA polymerase (GoldStar, Eurogentec, Belgium). PCR parameters were 2 min. at 94° C., 2 min. at 54° C. (5' region) or 64° C. (3'region), 1.3 min. at 72° C., 30 cycles (Thermojet thermal cycler, Eurogentec).

Figure 2:
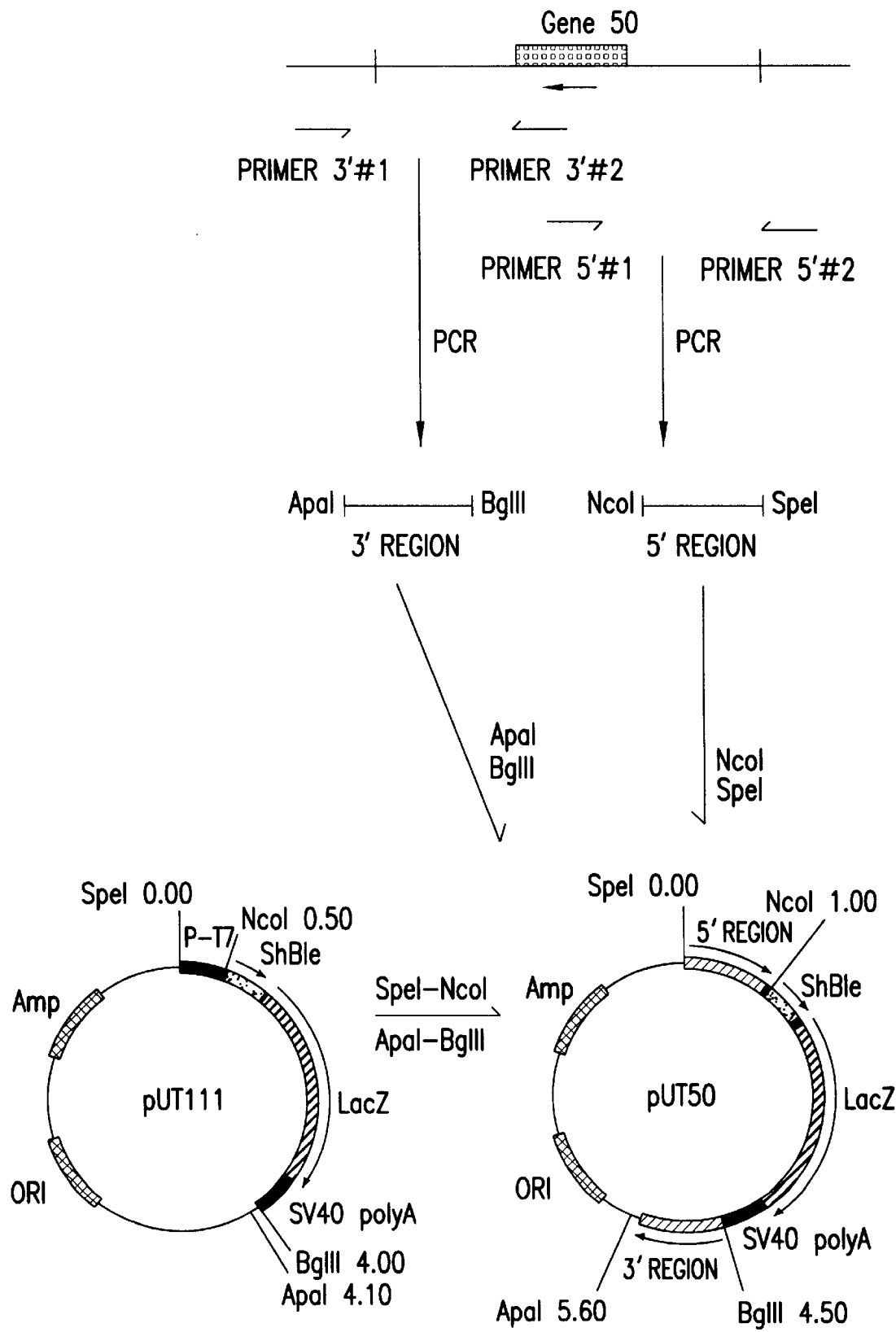
FIG. 2 is a schematic illustration of the construction of transfer plasmid pUT50 of the invention.

Both PCR products were cloned sequentially (FIG. 2) in plasmid pUT111 (Cayla, France). Plasmid pUT111 contains the lacZ gene of *E. coli* expressed as a 3' fusion protein with the product of the Sh-ble gene (bleomycin-resistance gene, cloned from *Streptoalloteichus hindustanus*) (Drocourt et al., 1990; Gatignol et al., 1988) under the transcriptional control of the constitutive, synthetic *E. coli*-(EM-7) promoter and the SV40 polyadenylation signal. The PCR product of region 5' obtained using primers 5' #1 and 2 were digested by the restriction endonucleases SpeI (site present in primer 5' #2) and NcoI (site present in primer 5' #1) and cloned in plasmid pUT1 11 digested by the same enzymes. The resulting plasmid and the PCR product of region 3' were digested by BgIII and ApaI and ligated. Region 3' was amplified using primers 3' #1 (which contains an ApaI site) and #2 (which contains a BgIII site). The resulting plasmid was designated pUT50. In this transfer plasmid, the EM-7 promoter was deleted and replaced by the putative promoter of gene 50.

Before constructing the recombinant virus, we determined if lacZ expression driven by the cloned putative gene 50 promoter could be sufficient be detectable in vitro. Indeed, the selection procedure implies the visual screening of plaques made under agarose containing X-gal and isolation of blue plaques as recombinant CCV. BB cells were transfected by electroporation with plasmids pUT50 or pCMVβ (Clontech, USA) as positive control. Plasmid pCMVβ expresses the lacZ gene under the transcriptional control of the human cytomegalovirus (HCMV) immediate-early gene promoter/enhancer. The plasmids used for transfection experiments were purified by equilibrium centrifugation in CsCl-ethidium bromide gradient and removal of residual RNA by centrifugation through 1M NaCl (Sambrook et al., 1989). Plasmid DNA was further extracted by phenolchloroform and concentrated by ethanol precipitation. 10 $\mu$g of purified plasmid was mixed in an electroporation cuvette with $2\times10^6$ trypsinized BB cells in 400 $\mu$l of culture medium. To optimize transfection efficiency, different pulse conditions were tested in BB cells first with pCMVβ, in order to obtain maximum yields of β-galactosidase activity, quantified by the ONPG assay (Sambrook et al., 1989). One optimized pulse condition (a single pulse of 1200 $\mu$Farad, 240 Volt and infinite resistance (Easyject+, Eurogentic)) was chosen and used for transfection. Directly after the pulse, 2.6 ml of culture medium was added to the cells which were distributed in 3 wells of a 24-well plate. Transfected cells were harvested after 24 h, 48 h, and 72 h and β-galactosidase activity measured by the ONPG assay. LacZ expression was only detected with the control pCMVβ. The lack of detectable expression of β-galactosidase with pUT50 indicated that the putative promoter of gene 50 was not able to direct expression of the reporter lacZ gene. This could result from promoter strength being weak or from the absence of transactivating viral gene products. To assess this latter possibility, transfected cells were subsequently infected with CCV. Twenty-hours after their transfection with plasmids pUT50 or pCMVβ, BB cells were infected with CCV at a MOI of 1 and incubated for an additional 48 hours. β-galactosidase activity could be detected in these conditions with both plasmids although about 10 times weaker with pUT50 than with pCMVβ. Thus, the cloned promoter of gene 50 can direct expression of the lacZ reporter gene in the presence of viral gene products to a level which should be sufficient to allow the visual isolation of a recombinant CCV.

Step 2. Isolation of the Recombinant CCVd150

The second step for constructing the recombinant CCV involved the homologous recombination between the plasmid pUT50 and the viral DNA.

CCO cells (channel catfish ovary cell line) grown at 30° C. in Dulbecco's modified minimal essential medium (DMEM) supplemented with 10% fetal bovine serum, 25 mM HEPES buffer, 100 IU/ml penicillin and 100 $\mu$g/ml streptomycin were used for producing the recombinant virus. Infectious viral DNA was purified by sodium iodide gradient centrifugation (Hanson et al., 1994). Transfer plasmid pUT50 was purified by equilibrium centrifugation in CsCl-ethidium bromide gradient as described above, linearized by treatment with restriction endonuclease SpeI and purified by phenol-chloroform extraction. CCO cells were cotransfected with 10 μg of purified CCV DNA and 7 μg of pUT50 DNA using the cationic liposome technique as described previously (Hanson et al., 1994). Briefly, both DNAs in a final volume of 100 μl were mixed with 50 μl Lipofectin (Gibco BRL) and incubated 20 min. on ice before addition of 3 ml of OPTIMEM I (Gibco BRL). A monolayer of CCO cells in 25 cm² tissue culture flask was washed three times with 1.5 ml of OPTIMEM I before being overlaid with the lipofectin-DNA complex. Twenty-four hours post transfection, 3 ml of DMEM and supplemented with 20% fetal bovine serum, 25 mM HEPES buffer, 200 IU/ml penicillin and 200 μg/ml streptomycin was added to the flask. Medium and cells were harvested when cytopathic effect involved the entire cell sheet. Infected cells were scraped in the medium, pelleted by centriougation (800 g, 10 min, 4° C.), sonicated and cell debris were removed by a second centrifgation (800 g, 10 min., 4° C.). Supeofatants from these two centriflgations were pooled and aliquots were stored at −70° C. For plaque purification of lacZ express ion virus 300 μl of ten-fold dilutions of the cotransfection supernatant were overlaid on CCO monolayers in 24-well plates. After a one hour incubation, cells were overlaid with 500 μl of cell culture medin containing 0.75% melted agarose and 300 ug/ml X-gal at 40° C. The plates were allowed to cool to room temperature and were then incubated at 30° C. Three blue plaques were picked, diluted in culture medium and submitted to five additional sequential plaque purification s under agarose overlay. Three CCV recombinants producing blue plaques were isolated. The viral progeny of each recombinant was evaluated for purity using Expand™ Long Template PCR System (Boehringer Mannheim) and primers chosen inside the flanking sequences of gene 50. Two primers [SEQ ID NOS.: 5–6] (62100+: 5'CTGTCTCCGATGACGCCGCATTGAT3' and 64653−: 5'tCGCGCTCGGAGCAGGGTTGTTAGCA3') were designed to amplify a fragment of 2553 bp in wild-type (wt) CCV or a fragment of 4140 bp in recombinant CCV. Recombinant virus was concentrated by a 30 min. centrifugation at 21000 g before use. PCR parameters included a pre-denaturation step 2 mi. at 94° C., then 35 cycles of 10 sec. at 94° C., 30 sec. at 61° C., 2 min. at 68° C. with an incremental increase of 20 sec. per cycle starting at cycle eleven. Two recombinants (designated 1.1.5 and 3.1.4) were free of wt contamination whereas one recombinant (designated 4.4.4) was still contaminated as evidenced by the presence of both amplification products. The 1.1.5. recombinant was chosen for further analysis and designated CCVd150.

Characterization of the Recombinant CCVd150

A Southern blotting experiment was performed to confirm the replacement of gene 50 by the lacZ gene of *E. coli*. Viral DNA was prepared as follows: three 175-cm² tissue culture flasks were infected with wt or CCVd150 in culture medium. When cytopathic effect was generalized, medium was clarified by a 20 min. centrifugation at 800 g at 4° C. and virus was subsequently pelleted by a one hour centrifugation at 50000 g at 4° C. Viral pellets were suspended and incubated 30 min. at room temperature in 15 ml TE buffer (Tris 10 mM, EDTA 1 mM, pH 8) supplemented with 0.1% NP40. Viral DNA was pelleted by centrifugation (100,000 g, 2 h at 4° C.) through 5 ml of sucrose 30% and resuspended in 450 μl of TE buffer. Proteins were removed by a 2 h incubation in the presence of 1% SDS and 100 μg/ml proteinase K. After 3 extractions with phenol/chloroform, viral DNA was precipitated with ethanol and sodium acetate and resuspended in TE buffer. Four μg of CCVd150 and wt CCV DNA were digested with the restriction endonuclease AseI and restriction fragments were separated on a 0.7% agarose gel, stained with ethidium bromide and visualized under UV light. The 8669 bp fragment spanning nt 69547 to nt 78216 in wt CCV was replaced by a fragment of 10252 bp in the recombinant virus corresponding to the Sh-ble-lacZ fusion gene. The gel was blotted onto nylon Hybond-N membrane (Amersham) and hybridization was performed using a random primed digoxigenin-labeled lacZ gene probe in a non-radiographic detection system (DIG High Prime Labeling and Detection Kit, Boehringer Mannheim), according to the manufacturer's instructions. The 10252 bp fragment in CCVd150 hybridized to the lacZ specific probe.

After [2-³H] D-mannose labeling (Vandeiheijden, et al., 1999) gp 250 was not detected in the culture medium of BB cells infected with CCVd150, confirming the lack of expression of the glycoprotein associated with gene 50 that was replaced by the *E. coli* LacZ gene in the recombinant virus.

Figure 3:
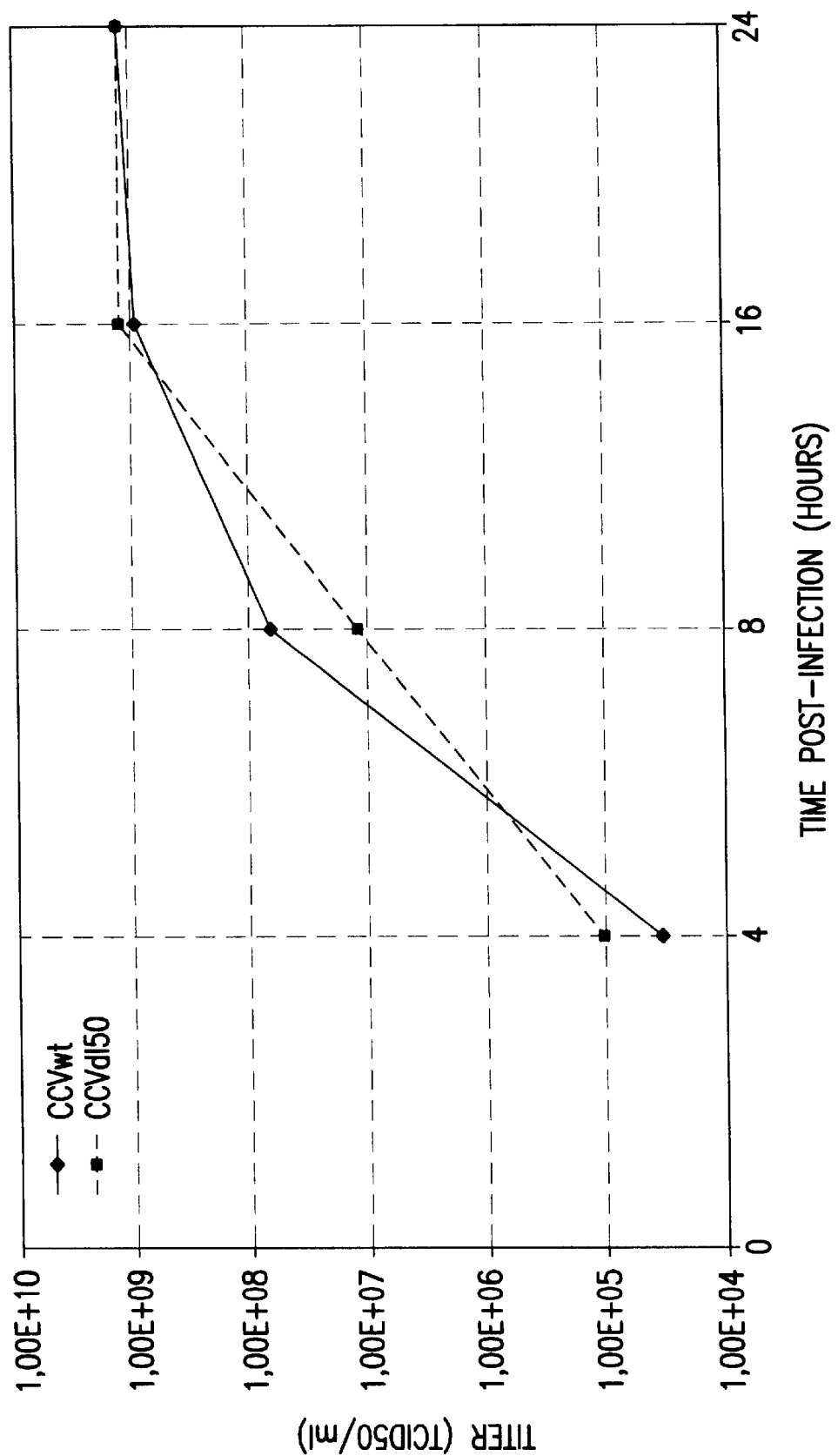
FIG. 3 is a growth curve comparing growth of wild-type and gene 50 deleted recombinant channel catfish virus in BB cells.

The ability of the recombinant to replicate in BB cells was assessed using a one step growth curve. Wt CCV and CCVd150 were inoculated at 2 TCID50/cell into a 24-well plate containing monolayers of BB cells. Virus was allowed to absorb for 1 hr at 28° C. The wells were then rinsed with 500 μl of MEM, overlaid with 300 μl of culture medium and incubated at 28° C. Every four hours, infected cells were collected in the medium, pelleted by a 10 min. centrifugation at 600 g, laced by 3 cycles of freeze-thawing and pooled with the corresponding supernatants. Virus titers were determined by end-point dilution and expressed as $TCID_{50}$/ml (Reed and Muench, 1938). In vitro, both wt and d150 viruses possessed similar growth kinetics, indicating that gene 50 is not implicated in virus replication (FIG. 3).

CCV infected cell culture supernatants were examined for the presence of secreted viral glycoproteins. Cells were infected with the wild-type strain, the attenuated V60 strain or the recombinant CCVd150 and labeled with [³H]mannose to detect N-glycosylated proteins. Confluent monolayers of BB cells in 24-well plates were infected with the virus (MOI=2) in culture medium without fetal bovine serum. Medium was removed after virus absorption (1 hr. at 28° C.) and cells were incubated for 20 hr in 300 μl of MEM with Earle's salts without glucose (Gibco BRL), supplemented with 0.3 g/L D(+)glucose, penicillin/streptomycin, L-glutamine and 150 μCi/ml of [2-³H] D-mannose (specific activity 25 Ci/mmole, ICN-Flow). Infected cells were collected with the medium at 20 hr post-infection (p.i.) and pelleted by a 10 min. centrifugation at 600 g. The supernatant was further centrifuged at 15,000 g for 2 hr at 4° C. to pellet and remove labeled virus. Supernatant from this last step (supernatant fraction) was used to analyze secreted products. Supernatant samples (10 μl) were mixed with an equal volume of 2×concentrated loading buffer, boiled for 5 min., and submitted to SDS-PAGE (Mighty Small II electrophoresis system, Hoefer Scientific Instruments) as described in Sambrook et al., 1989. After electrophoresis, gels were fixed in a 7% acetic acid solution, rinsed in distilled water and evaluated by fluorography by soaking the gels in a 1 M sodium salicylate solution in 40% ethanol, drying under vacuum and exposing MP film (Amersham, U.K.) to the gels at −70° C. for one week. A strongly labeled band of apparent molecular mass superior to 200 kDa (designated gp250) was detected in the wt sample while it was absent in the V60 strain and CCVd150 samples. However, a strongly labeled band was observed migrating as a 135 kDa glycoprotein (designated gp135) in the V60 strain sample but absent in the wt, in the CCVd150 or in the mock-infected cell samples. Except for gp250 and gp135, the other glycoproteins observed in wt, V60 and CCVd150 supematants were also present in the mock infected cell supernatant and thus do not represent virus specific products. The protein encoded by gene 50 protein is likely to be heavily N-glycosylated (35 potential sites) but also 0-glycosylated. The attenuated V60 strain of CCV possesses a deletion of 388 amino acids in the central domain of the ORF50 protein, encompassing most of the potential 0- and 24 N-glycosylation sites (Vanderheijden et al. 1996). This major deletion should increase the relative mobility in SDS-PAGE of the glycoprotein encoded by ORF50 in the V60 strain. Although the calculated molecular mass of the ORF50 protein is 64 kDa, the presence of sugars can substantially reduce the mobility of glycoproteins in SDS-PAGE analysis. Consequently, we postulated that ORF50 encodes gp250 in the wt and that the deletion in the V60 strain ORF50 leads to gp135, the truncated version of gp250. In the recombinant CCVd150, the lacZ gene of *E. coli* replaces gene 50 and therefore, gp250 is not produced, as observed above.

In Vivo Tests

Channel catfish fingerlings were exposed to various levels of CCV or CCVd150 by immersion challenge and virus induced mortality, CCV neutralizing antibodies and antibodies to β-galactosidase were determined. These in vivo tests consisted of replicate tanks of 15 fish as follows: 6 replicates exposed to $3 \times 10^4$ PFU of CCV, 5 replicates exposed to $3 \times 10^4$ PFU of CCVD150, 5 replicates exposed to $3 \times 10^5$ PFU of CCVd150, 6 replicates exposed to $3 \times 10^6$ PFU of CCVd150, 5 replicates exposed to $3 \times 10^7$ PFU of CCVd150 and 2 replicates exposed to no virus (negative controls). Fish were exposed to virus in 400 ml of water for 30 minutes and then placed in 40 L polypropylene tanks receiving 4 L/h dechlorinated city tap water. Dead fish were counted, removed and posterior kidney extracts were cultured on CCO cells to confirm CCVD as the cause of death. After 15 days fish from the control tanks, CCV exposed tanks and $3 \times 10^7$ PFU CCVd150 exposed tanks were bled and serum evaluated for CCV neutralizing antibodies and for antibodies to β-galactosidase using ELISA (Zhang and Hanson, 1996).

Fish were anesthetized with 100 mg/l tricane methane sulfonate, the coudal peduncle was severed and blood was collected from the caudal vein into microcentrifuge tubes. Serum was extracted and stored at −70° C. until analyzed. Serum was heat inactivated at 45° C. for 30 min. Neutralization assays were performed in triplicate using 1:4 serial dilutions in 15 μl volumes using MBSS as the diluent. Then 15 μl of HBSS containing 30 PFU of CCV was added to each dilution and the mixture incubated at 30° C. for 1 hr. Each sample was then added to a well of a 24 well plate containing $4 \times 10^2$ of trypsinized CCO cells in 1 ml of medium. The plates were then incubated at 30° C. for 24 hr., fixed with 10% formalin, stained with crystal violet and plaques counted. Titers are reported as the calculated dilution resulting in 50% plaque reduction calculated using the method of Karber (1931). CCV exposed fish experienced 72% ±18% (mean ISD) CCVD associated mortality while none of the CCVd150 exposed fish (even those exposed to 1000×the dose of the CCV group) or controls died from CCVD The 50% neutralizing titer for $3 \times 10^7$ PFU CCVd150 exposed fish was 0.0114±0.0039. No neutralization was evident in 1:5 dilution or serum from negative control fish. The CCV exposed survivors had a titer of 0.0047. The mean OD for β-galactosidase specific antibodies of the $3 \times 10^7$ PFU CCVd150 exposed fish was 2.89±0.56 compared to 0.25 in the control fish. These results show that the recombinant virus is attenuated and induced virus specific immunity as well as an immune response to the inserted gene product.

References

1. Awad, M. A., Nusbaum, K. E., and Brady, Y. J. (1989). Preliminary studies of a newly developed subunit vaccine for channel catfish virus disease. Journal of aquatic animal health, 1, 233–237.

2. Davison, A. J. (1992). Channel Catfish Virus: A new type of herpesvirus. Virology, 186, 9–14.

3. Drocourt, D., Calmels, T., Reynes, J. P., Baron, M. and Tiraby, G. (1990). Cassettes of the Streptoalloteichus hindustanus ble gene for transformation of lower and higher eukaryotes to phleomycin resistance. Nucl. Acids Res., 18, 4009.

4. Figan, N. (1968). Progress report on acute mortality of channel catfish fingerlings caused by a virus. Bull. Off. Int. Epiz., 69, 1167–1168.

5. Gatignol, A., Durand, H., and Tiraby, G. (1988). Bleomycin resistance conferred by a drug binding protein. FEBS Letters, 230, 171–0175.

6. Hartmann, J. X. and Noga, E. J. (1980). Channel catfish virus disease vaccine and method of preparation thereof and method of immunization therewith. U.S. Pat. No. 4,219,543.

7. Hanson, L. A., Kousoulas, K. G., and Thune, R. L. (1994). Channel catfish herpesvirus (CCV) encodes a functional thymidine kinase gene: elucidation of a point mutation that confers resistance to Ara-T. Virology, 202, 659–664.

8. Karber, G. 1931. Beitrag zur kollektiven Behandlung phannakologischer Reihenversuche. Naunyn-Schimiedebergs Archiv feur experimentalle Pathologie und Phannakologie 162: 480–483.

9. Noga, E. J. and Hartmann, J. X. (1981). Establishment of walking catfish (Clarias batrachus) cell lines and development of a channel catfish (Ictalurus punctatus) virus vaccine. Can. J. Fish. Aquat. Sci., 38, 925–930.

10. Plumb, J. A. (1978). Epizootiology of channel catfish virus disease. U.S. National Marine Fisheries Service Marine Fisheries Review, 40, 26–29.

11. Randall, R. E., Killington, R. A., and Watson, D. H. (1980). Glycoproteins with type common and type specific antigenic sites excreted from cells infected with herpes simplex virus types 1 and 2. J. Gen. Virol, 48, 297–310.

12. Reed, L. J. and Muench, H. (1938). A simple method of estimating fifty percent endpoints. Amer. J. Hygiene, 27, 493–497.

13. Sambrook, J., Fritsch, E. F., and Maniatis, T. (1989). Molecular cloning, a laboratory manual. $2^{nd}$ edition. Cold Spring Harbor Laboratory Press, USA.

14. Vanderheijden, N., Alard, P., Lecomte, C. and Martial, J. A. (1996). The attenuated V60 strain of channel catfish virus possesses a deletion in ORF50 coding for a potentially secreted glycoprotein. Virology, 218, 422–426.

15. Vanderheijden, N., Hawson, L. A., Thiry, E., and Martia, J. A. (1999). Channel catfish virus gene so encodes a secreted, mucin-like glycoprotein. Virology, 257, 220–227.

16. Walczak, E. M., Noga, E. J., and Hartnann, J. X. (1981). Properties of a vaccine for channel catfish virus disease and a method of administration. Develop. Biol. Standard, 49, 419–429.

17. Zhang, H. G., and Hanson, L. A. (1995). Deletion of thymidine kinase gene attenuates channel catfish herpesvirus while maintaining infectivity. Virology, 209, 658–663.

18. Zhang, H. G. and Hanson, L. A. (1996). Recombinant channel catfish virus (Ictalurid herpesvirus 1) can express foreign genes and induce antibody production against the gene product. Journal of Fish Diseases, 19, 121–128.

The invention of this application is described above generically, and in terms of specific examples. The examples are not intended as, as should not be construed as, limiting unless specifically so indicated. Variations will occur to those of ordinary skill in the art in the practice of this invention, beyond these specific examples provided, which remain within the scope of this invention as claimed below. Thus, alternative reporter genes, inserts for gene 50, or simple deletion of gene 50 are all enabled by the disclosure herein, and remain within the scope of the invention. Similarly, methods of vaccination, or alternative routes of treatment, beyond those specifically described herein will be familiar to those of skill in the art. These variations remain within the scope of the invention, unless specifically excluded by the recitations of the claims below.

What is claimed:

1. A recombinant channel catfish virus (CCV) that does not produce a functional gene 50 glycoprotein as a result of a deletion or insertion in gene 50;
   wherein said recombinant CCV is substantially similar to wt CCV except for the deletion of gene 50.

2. The virus of claim 1, wherein said CCV, when administered to channel catfish, is avirulent and induces antibody generation, wherein said antibodies bind to CCV.

3. The virus of claim 1, wherein gene 50 is replaced by genetic material not found in wt CCV.

4. The virus of claim 1, wherein gene 50 is replaced by a reporter gene.

5. A CCV vaccine, comprising an effective amount of the recombinant virus of Claim 1.

6. The vaccine of claim 5, wherein said vaccine comprises a carrier suitable for parenteral administration to catfish.

7. The vaccine of claim 5, wherein said vaccine comprises a carrier suitable for water-borne administration of said recombinant virus.

8. A method of vaccinating channel catfish to prevent mortality due to CCV disease, comprising vaccinating said catfish with the vaccine of claim 5.

* * * * *

UNITED STATES PATENT AND TRADEMARK OFFICE
CERTIFICATE OF CORRECTION

PATENT NO. : 6,322,793 B1
DATED : November 27, 2001
INVENTOR(S) : Nathalie Vanderheijden et al.

It is certified that error appears in the above-identified patent and that said Letters Patent is hereby corrected as shown below:

Title page,
Item [75], Inventors: "Nathalie Vanderheijden, Brussels; Joseph A. Martial, Esneux, both of (BE); Larry A. Hanson, Mississippi State, MS (US)" should read -- Nathalie Vanderheijden, Merelbeke; Joseph A. Martial, Modave, both of (BE); Larry A. Hanson, Mississippi State, MS (US) --

Item [56], References Cited: please insert the following:
-- This invention was made with U.S. Government support under contract number 94-37204-0853 awarded by the Department of Agriculture. The U.S. Government may have certain rights in this invention. --
"The Audobon Society Nature Guides:" should read -- The Audubon Society Nature Guides: --

Item [57], ABSTRACT,
Line 22, "provides a vaccine with" should read -- provides a vaccine --.

Column 1,
Line 43, "Vanderhejiden" should read -- Vanderheijden --.
Line 48, "viral cycle by is still unclear." should read -- viral cycle is still unclear. --.

Column 2,
Line 64, "CCVdl50" should read -- CCVdl50 --.

Column 3,
Line 29, "flanlkng" should read -- flanking --.
Line 54, "$(NH_4)_2S_4$," should read -- $(NH_4)_2SO_4$, --.

Column 4,
Line 3, "pUT1 11" should read -- pUT111 --.
Line 13, "could be sufficient be detectable" should read -- could be sufficient to be detectable --.
Line 34, "Eurogentic" should read -- Eurogentec --.
Line 57, "CCVdl50" should read -- CCVdl50 --.

UNITED STATES PATENT AND TRADEMARK OFFICE
CERTIFICATE OF CORRECTION

PATENT NO.      : 6,322,793 B1
DATED           : November 27, 2001
INVENTOR(S)     : Nathalie Vanderheijden et al.

It is certified that error appears in the above-identified patent and that said Letters Patent is hereby corrected as shown below:

Column 5,
Line 19, "centriougation" should read -- centrifugation --.
Line 21, "centrifgation" should read -- centrifugation --.
Line 21, "Supeofatants" should read -- Supernatants --.
Line 22, "centriflgations" should read -- centrifugations --.
Line 27, "medin" should read -- medium --.
Line 39, "5'tCGCGCTCGGAGCAGGGTTGTTAGCA3'" should read
-- 5'CGCGCTCGGAGCAGGGTTGTTAGCA3' --
Line 44, "mi." should read -- min. --.
Line 52, "CCVd150." should read -- CCVdl50. --.
Lines 53 and 57, "CCVd150" should read -- CCVdl50 --.

Column 6,
Lines 3, 16, 19, 24, 39 and 66, "CCVd150" should read -- CCVdl50 --.
Line 17, "Vandeiheijden" should read -- Vanderheijden --.
Line 30, "laced" should read -- lysed --.

Column 7,
Lines 2, 4, 21, 26, 31, 32, 41 and 62, "CCVd150" should read -- CCVdl50 --.
Line 5, "supematants" should read -- supernatants --.
Line 33, "CCVd150" should read -- CCVDl50 --. Both occurrences.
Line 46, "coudal" should read -- caudal --.
Line 51, "MBSS" should read -- HBSS --.
Line 61, "mean ISD" should read -- mean ±SD --.
Line 64, "CCVd150" should read -- CCVdl50 --.
Line 66, "dilution or serum" should read -- dilution of serum --.

Column 8,
Line 2, "CCVd150" should read -- CCVdl50 --.
Line 20, "Figan" should read -- Fijan --.
Line 60, "Hawson" should read -- Hanson --.
Line 61, "Martis" should read -- Martial --.

UNITED STATES PATENT AND TRADEMARK OFFICE
CERTIFICATE OF CORRECTION

PATENT NO. : 6,322,793 B1
DATED : November 27, 2001
INVENTOR(S) : Nathalie Vanderheijden et al.

It is certified that error appears in the above-identified patent and that said Letters Patent is hereby corrected as shown below:

<u>Column 8 cont'd,</u>
Line 61, "gene so encodes" should read -- gene 50 encodes --.
Line 64, "Hartnann" should read -- Hartmann --.

Signed and Sealed this

Thirteenth Day of August, 2002

*Attest:*

JAMES E. ROGAN
*Attesting Officer*  *Director of the United States Patent and Trademark Office*

```
                        SEQUENCE LISTING

<160> NUMBER OF SEQ ID NOS: 6

<210> SEQ ID NO 1
<211> LENGTH: 34
<212> TYPE: DNA
<213> ORGANISM: Ictalurid herpesvirus 1

<400> SEQUENCE: 1
aatctagacc atggattatc aacacatgaa cgtc                         34

<210> SEQ ID NO 2
<211> LENGTH: 26
<212> TYPE: DNA
<213> ORGANISM: Ictalurid herpesvirus 1

<400> SEQUENCE: 2
ttactagttc gaggtcaagc tacgga                                  26

<210> SEQ ID NO 3
<211> LENGTH: 29
<212> TYPE: DNA
<213> ORGANISM: Ictalurid herpesvirus 1

<400> SEQUENCE: 3
attaagggcc cttggccggt gcggcgaag                               29

<210> SEQ ID NO 4
<211> LENGTH: 29
<212> TYPE: DNA
<213> ORGANISM: Ictalurid herpesvirus 1

<400> SEQUENCE: 4
attaaagatc taaccgcccc cgccggaga                               29

<210> SEQ ID NO 5
<211> LENGTH: 25
<212> TYPE: DNA
<213> ORGANISM: Ictalurid herpesvirus 1

<400> SEQUENCE: 5
ctgtctccga tgacgccgca ttgat                                   25

<210> SEQ ID NO 6
<211> LENGTH: 25
<212> TYPE: DNA
<213> ORGANISM: Ictalurid herpesvirus 1

<400> SEQUENCE: 6
cgcgctcgga gcagggttgt tagca                                   25
```